(12) United States Patent
Shimizukawa

(10) Patent No.: US 11,382,579 B2
(45) Date of Patent: Jul. 12, 2022

(54) RADIOGRAPHY APPARATUS COMPRISING DETECTION UNIT DETECTING AT LEAST A DIRECTION OF A RADIATION DETECTOR AND DISPLAY UNIT DISPLAYING DIRECTION INFORMATION, RADIOGRAPHY METHOD, AND RADIOGRAPHY PROGRAM

(71) Applicant: FUJIFILM Corporation, Tokyo (JP)

(72) Inventor: Sho Shimizukawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 109 days.

(21) Appl. No.: 16/568,790

(22) Filed: Sep. 12, 2019

(65) Prior Publication Data
US 2020/0100743 A1 Apr. 2, 2020

(30) Foreign Application Priority Data
Sep. 27, 2018 (JP) .............................. JP2018-182733

(51) Int. Cl.
*A61B 6/00* (2006.01)
(52) U.S. Cl.
CPC .......... *A61B 6/4283* (2013.01); *A61B 6/4085* (2013.01); *A61B 6/42* (2013.01);
(Continued)
(58) Field of Classification Search
CPC ....... A61B 6/42; A61B 6/4208; A61B 6/4233; A61B 6/4266; A61B 6/4283; A61B 6/44;
(Continued)

(56) References Cited

U.S. PATENT DOCUMENTS

| 7,545,914 B2* | 6/2009 | Kito | ..................... A61B 6/4494 378/207 |
| 7,581,885 B2* | 9/2009 | Ertel | ....................... A61B 6/08 378/204 |

(Continued)

FOREIGN PATENT DOCUMENTS

| JP | 2003-14848 A | 1/2003 |
| JP | 2003-52677 A | 2/2003 |

(Continued)

OTHER PUBLICATIONS

An English Translation of JP2012024387A by Patent Translate. (Year: 2022).*

(Continued)

*Primary Examiner* — Allen C. Ho
(74) *Attorney, Agent, or Firm* — Birch, Stewart, Kolasch & Birch, LLP

(57) ABSTRACT

A radiation detector that generates and outputs image data representing a radiographic image corresponding to emitted radiation, and up and down directions of the radiation detector are set in advance with respect to top and bottom directions of the radiographic image, a detection unit that detects at least one direction of the up or down directions of the radiation detector, and a display unit that is provided in a housing for accommodating the radiation detector and displays direction information representing the at least one direction of the up and down directions of the radiation detector detected by the detection unit are included.

13 Claims, 10 Drawing Sheets

(52) U.S. Cl.
CPC .......... *A61B 6/4208* (2013.01); *A61B 6/4233* (2013.01); *A61B 6/44* (2013.01); *A61B 6/4411* (2013.01); *A61B 6/4452* (2013.01); *A61B 6/461* (2013.01); *A61B 6/463* (2013.01); *A61B 6/464* (2013.01); *A61B 6/467* (2013.01); *A61B 6/5294* (2013.01); *A61B 6/542* (2013.01); *A61B 6/545* (2013.01); *A61B 6/587* (2013.01)

(58) Field of Classification Search
CPC ....... A61B 6/4411; A61B 6/4452; A61B 6/46; A61B 6/461; A61B 6/463; A61B 6/464; A61B 6/465; A61B 6/467; A61B 6/52; A61B 6/5294; A61B 6/54; A61B 6/542; A61B 6/545; A61B 6/547; A61B 6/587
USPC .................. 378/91, 98, 98.8, 189, 205, 207; 250/370.09
See application file for complete search history.

(56) References Cited

U.S. PATENT DOCUMENTS

| | | | | |
|---|---|---|---|---|
| 7,590,221 | B2* | 9/2009 | Durack | A61B 6/4283 |
| | | | | 378/162 |
| 8,690,426 | B2* | 4/2014 | Liu | G03B 42/02 |
| | | | | 378/205 |
| 8,742,354 | B2* | 6/2014 | Shimizukawa | A61B 6/548 |
| | | | | 250/354.1 |
| 9,050,051 | B2* | 6/2015 | Nakatsugawa | G03B 42/04 |
| 9,134,436 | B2* | 9/2015 | Kwak | G01T 1/175 |
| 9,314,216 | B2* | 4/2016 | De Godzinsky | A61B 6/06 |
| 9,314,217 | B2* | 4/2016 | De Godzinsky | A61B 6/145 |
| 9,386,959 | B2* | 7/2016 | Lee | A61B 6/545 |
| 9,649,080 | B2* | 5/2017 | Kwak | A61B 6/488 |
| 9,730,656 | B2* | 8/2017 | Hyde | H01L 27/14806 |
| 9,778,380 | B2* | 10/2017 | Enomoto | G01T 1/161 |
| 9,788,810 | B2* | 10/2017 | Ancar | A61B 6/542 |
| 9,907,530 | B2* | 3/2018 | Charnegie | A61B 6/4494 |
| 9,931,089 | B2* | 4/2018 | Nariyuki | A61B 6/467 |
| 9,968,315 | B2* | 5/2018 | Ogura | A61B 6/4283 |
| 9,986,964 | B2* | 6/2018 | Kravis | A61B 6/5205 |
| 9,993,221 | B2* | 6/2018 | Kim | A61B 6/06 |
| 10,080,542 | B2* | 9/2018 | Kwak | G01B 7/30 |
| 10,085,710 | B2* | 10/2018 | Suzuki | A61B 6/547 |
| 10,098,609 | B2* | 10/2018 | Kim | A61B 6/06 |
| 10,100,974 | B2* | 10/2018 | Fütterer | F16M 11/18 |
| 10,111,642 | B2* | 10/2018 | Deinlein | A61B 6/547 |
| 10,149,659 | B1* | 12/2018 | Schwartz | A61B 6/56 |
| 10,213,180 | B2* | 2/2019 | Kravis | A61B 6/145 |
| 10,258,307 | B2* | 4/2019 | Park | A61B 6/547 |
| 10,299,741 | B2* | 5/2019 | Kravis | A61B 6/467 |
| 10,299,742 | B2* | 5/2019 | Kravis | G06F 11/0754 |
| 10,617,380 | B2* | 4/2020 | Tagawa | A61B 6/46 |
| 10,653,385 | B2* | 5/2020 | Mehendale | A61B 6/587 |
| 10,660,584 | B2* | 5/2020 | Tajima | A61B 6/10 |
| 10,709,406 | B2* | 7/2020 | Aoshima | A61B 6/42 |
| 10,736,600 | B2* | 8/2020 | Allen | A61B 6/56 |
| 10,743,822 | B2* | 8/2020 | Simon | A61B 6/025 |
| 10,806,412 | B2* | 10/2020 | Imamura | A61B 6/467 |
| 10,898,156 | B2* | 1/2021 | Nebosis | A61B 6/4405 |
| 10,925,555 | B2* | 2/2021 | Imamura | A61B 6/465 |
| 10,939,884 | B2* | 3/2021 | Nariyuki | A61B 6/58 |
| 2015/0276944 | A1 | 10/2015 | Enomoto et al. | |

FOREIGN PATENT DOCUMENTS

| | | |
|---|---|---|
| JP | 2007-37837 A | 2/2007 |
| JP | 2010-240141 A | 10/2010 |
| JP | 2012-24387 A | 2/2012 |
| JP | 2015-190925 A | 11/2015 |
| JP | 6170863 B2 | 7/2017 |
| WO | WO 2010/134365 A1 | 11/2010 |

OTHER PUBLICATIONS

An English Translation of JP2003052677A by Patent Translate. (Year: 2022).*
An English Translation of JP2003014848A by Patent Translate. (Year: 2022).*
Japanese Notice of Reasons for Refusal for Japanese Application No. 2018-182733, dated Feb. 22, 2022, with an English translation.
Japanese Office Action for Japanese Application No. 2018-182733, dated Aug. 10, 2021, with English translation.

* cited by examiner

RADIOGRAPHY APPARATUS COMPRISING DETECTION UNIT DETECTING AT LEAST A DIRECTION OF A RADIATION DETECTOR AND DISPLAY UNIT DISPLAYING DIRECTION INFORMATION, RADIOGRAPHY METHOD, AND RADIOGRAPHY PROGRAM

CROSS-REFERENCE TO RELATED APPLICATION

This application claims priority from Japanese Patent Application No. 2018-182733, filed on Sep. 27, 2018, the disclosure of which is incorporated by reference herein in its entirety.

BACKGROUND

Field of the Invention

The present disclosure relates to a radiography apparatus, a radiography method, and a radiography program.

Related Art

In JP6170863B, an electronic cassette comprising a sensor panel that has a rectangular imaging area and detects a radiographic image of a subject, a housing that houses the sensor panel, an operation unit disposed in the housing, an upper or lower setting unit that sets any one side of at least two adjacent sides of the four sides of the imaging area to an upper part or a lower part in the display posture of the radiographic image based on an operation instruction from the operation unit, a display unit that is disposed in the housing and displays a position of the upper part or the lower part of the radiographic image set by the upper or lower setting unit, and a memory that stores the upper or lower setting information by the upper or lower setting unit and the radiographic image in association with each other is proposed.

In addition, in JP2007-037837A and JP2010-240141A, a technique of detecting and displaying a direction of gravity in the imaging of a radiographic image is proposed since a state of the organ and a state of a contrast agent are changed by the influence of gravity and the gravity affects a subject.

However, in JP6170863B, since a technician operates a button provided on a radiography apparatus to perform an instruction of the up or down direction, there is room for improvement in consideration of the usability of the technician.

In addition, as in JP2007-037837A and JP2010-240141A, there is room for improvement with respect to the improvement of the usability of the technician, without considering the influence of gravity affecting the subject.

SUMMARY

This disclosure is made in consideration of the above facts, and an object of this disclosure is to provide a radiography apparatus, a radiography method, and a radiography program capable of improving the usability of the technician.

In order to achieve the above object, according to an aspect of the present disclosure, there is provided a radiography apparatus comprising a radiation detector that generates and outputs image data representing a radiographic image corresponding to emitted radiation and whose up and down directions are set in advance with respect to top and bottom direction of the radiographic image; a detection unit that detects at least one direction of the up or down directions of the radiation detector; and a display unit that is provided in a housing for accommodating the radiation detector and displays direction information representing the at least one direction detected by the detection unit.

The radiography apparatus according to the aspect of the disclosure may further comprise a control unit that performs control to display the direction information on the display unit in a case where a direction of the housing does not change for a predetermined time or more.

The radiography apparatus according to the aspect of the disclosure may further comprise a control unit that performs control to display the direction information on the display unit in a case where registration of an imaging menu is accepted.

The radiography apparatus according to the aspect of the disclosure may further comprise an impact detection unit that detects an impact; and a control unit that performs control to display the direction information on the display unit in a case where a predetermined impact is detected by the impact detection unit.

In the radiography apparatus according to the aspect of the present disclosure, the predetermined impact may be at least one of an impact equal to or larger than a predetermined threshold value or an impact equal to or larger than a predetermined number of times.

The radiography apparatus according to the aspect of the disclosure may further comprise a control unit that performs control to display the direction information on the display unit in a case where emission of radiation is started.

The radiography apparatus according to the aspect of the disclosure may further comprise a transmission unit that transmits a detection result of the detection unit to an external apparatus.

In the radiography apparatus according to the aspect of the present disclosure, the transmission unit may transmit the detection result of the detection unit to the external apparatus by adding the detection result to the image data.

The radiography apparatus according to the aspect of the disclosure may further comprise a transmission unit that transmits a rotation instruction including a rotation direction and a rotation amount to an external apparatus in a case where the image data needs to be rotated from the detection result of the detection unit.

In the radiography apparatus according to the aspect of the present disclosure, the transmission unit may transmit the rotation instruction to the external apparatus by adding the rotation instruction to the image data.

The radiography apparatus according to the aspect of the disclosure may further comprise a control unit that performs control to prohibit the display of the direction information on the display unit in a case where the radiography apparatus is in an imaging table.

In order to achieve the above object, according to another aspect of the present disclosure, there is provided a radiography method in which a computer executes processing. The radiography method comprises detecting at least one direction of up or down directions of a radiation detector that generates and outputs image data representing a radiographic image corresponding to emitted radiation and whose up and down directions are set in advance with respect to the top and bottom direction of the radiographic image by a detection unit; and displaying the at least one direction detected by the detection unit on a display unit provided in a housing for accommodating the radiation detector.

In order to achieve the above object, according to still another aspect of the present disclosure, there is provided a radiography program that causes a computer to execute detecting at least one direction of up or down directions of a radiation detector that generates and outputs image data representing a radiographic image corresponding to emitted radiation and whose up and down directions are set in advance with respect to the top and bottom direction of the radiographic image by a detection unit; and displaying the at least one direction detected by the detection unit on a display unit provided in a housing for accommodating the radiation detector.

According to the disclosure, it is possible to obtain an effect of providing a radiography apparatus, a radiography method, and a radiography program capable of improving the usability of a technician.

DETAILED DESCRIPTION

Figure 1:
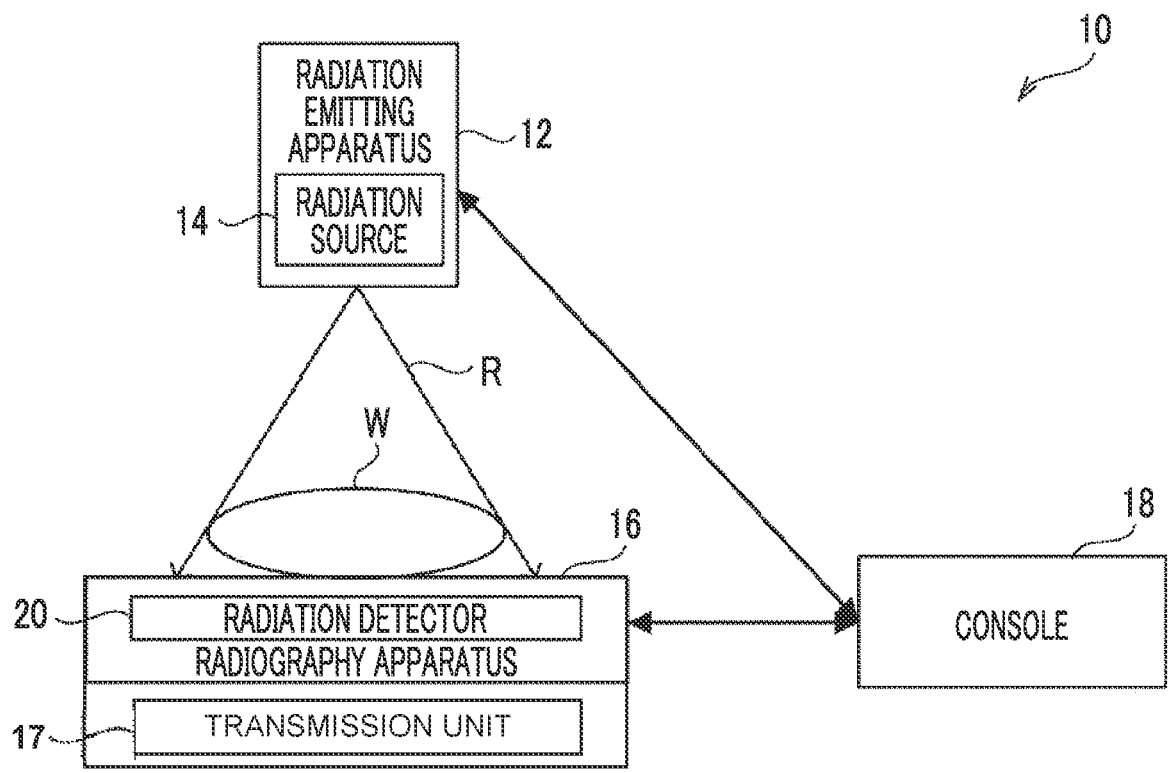
FIG. 1 is a block diagram showing an example of the configuration of a radiography system according to an embodiment.

First, the configuration of a radiography system 10 according to this embodiment will be described with reference to FIG. 1. As shown in FIG. 1, the radiography system 10 comprises a radiation emitting apparatus 12, a radiography apparatus 16, and a console 18.

The radiation emitting apparatus 12 according to this embodiment comprises a radiation source 14 that irradiates a subject W, which is an example of an imaging target, with radiation R such as X-rays. The radiation emitting apparatus 12 emits the radiation R with a cone beam shape. An example of the radiation emitting apparatus 12 is a treatment cart. A method for instructing the radiation emitting apparatus 12 to emit the radiation R is not particularly limited. For example, in a case where the radiation emitting apparatus 12 comprises an irradiation button, a user, such as a radiology technician, may perform the instruction to emit the radiation R using the irradiation button such that the radiation R is emitted from the radiation emitting apparatus 12. In addition, for example, the user, such as a radiology technician, may perform the instruction to emit the radiation R by operating the console 18 such that the radiation R is emitted from the radiation emitting apparatus 12.

In a case where the instruction to emit the radiation R is accepted, the radiation emitting apparatus 12 emits the radiation R from the radiation source 14 according to set emission conditions, such as a tube voltage, a tube current, and an emission period. Hereinafter, the dose of the radiation R is referred to as "the amount of radiation".

The radiography apparatus 16 according to this embodiment comprises a radiation detector 20 that detects the radiation R which is emitted from the radiation emitting apparatus 12 and then passes through the subject W. The radiography apparatus 16 captures a radiographic image of the subject W using the radiation detector 20.

Figure 2:
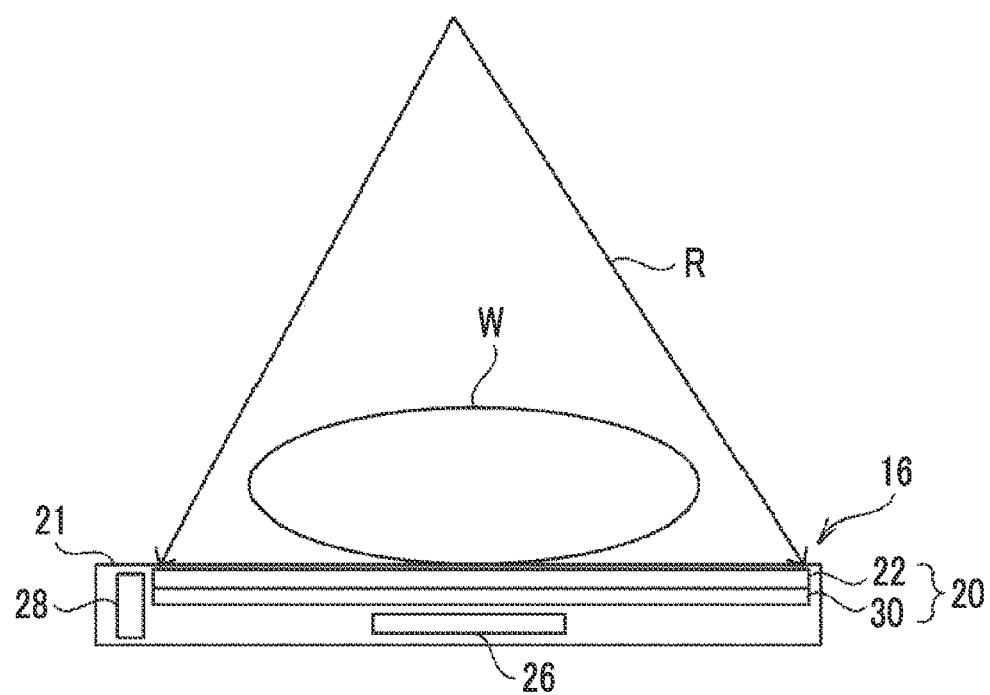
FIG. 2 is a side cross-sectional view of an example of the configuration of a radiography apparatus according to the embodiment.

Next, the configuration of the radiography apparatus 16 according to this embodiment will be described with reference to FIG. 2. As shown in FIG. 2, the radiography apparatus 16 comprises a plate-shaped housing 21 that passes the radiation R and has a waterproof, antibacterial, and airtight structure. The plate-shaped housing 21 includes the radiation detector 20, a control substrate 26, and a case 28.

The radiation detector 20 comprises a scintillator 22 which is an example of a light emitting layer that is irradiated with the radiation R and emits light and a thin film transistor (TFT) substrate 30. The scintillator 22 and the TFT substrate 30 are stacked in the order of the scintillator 22 and the TFT substrate 30 from the incident side of the radiation R.

That is, the radiation detector 20 is a so-called penetration side sampling (PSS) radiation detector on which the radiation R is incident from the scintillator 22.

The control substrate 26 is provided so as to correspond to the radiation detector 20 and electronic circuits, such as an image memory 56 and a control unit 58 which will be described below, are formed on the substrate. In addition, the control substrate 26 is disposed on the second side of the radiation detector 20 which is opposite to the incident side of the radiation R.

The case 28 is disposed at a position (that is, outside a range of an imaging region) that does not overlap the radiation detector 20 at one end of the plate-shaped housing 21 and houses a power supply unit 70 and the like described below. The installation position of the case 28 is not particularly limited, and, for example, the case 28 may be disposed at a position that overlaps the radiation detector 20 on the side of the radiation detector 20 which is opposite to the incident side of the radiation R.

Next, the configuration of a main part of an electrical system of the radiography apparatus 16 according to this embodiment will be described with reference to FIG. 3.

Figure 3:
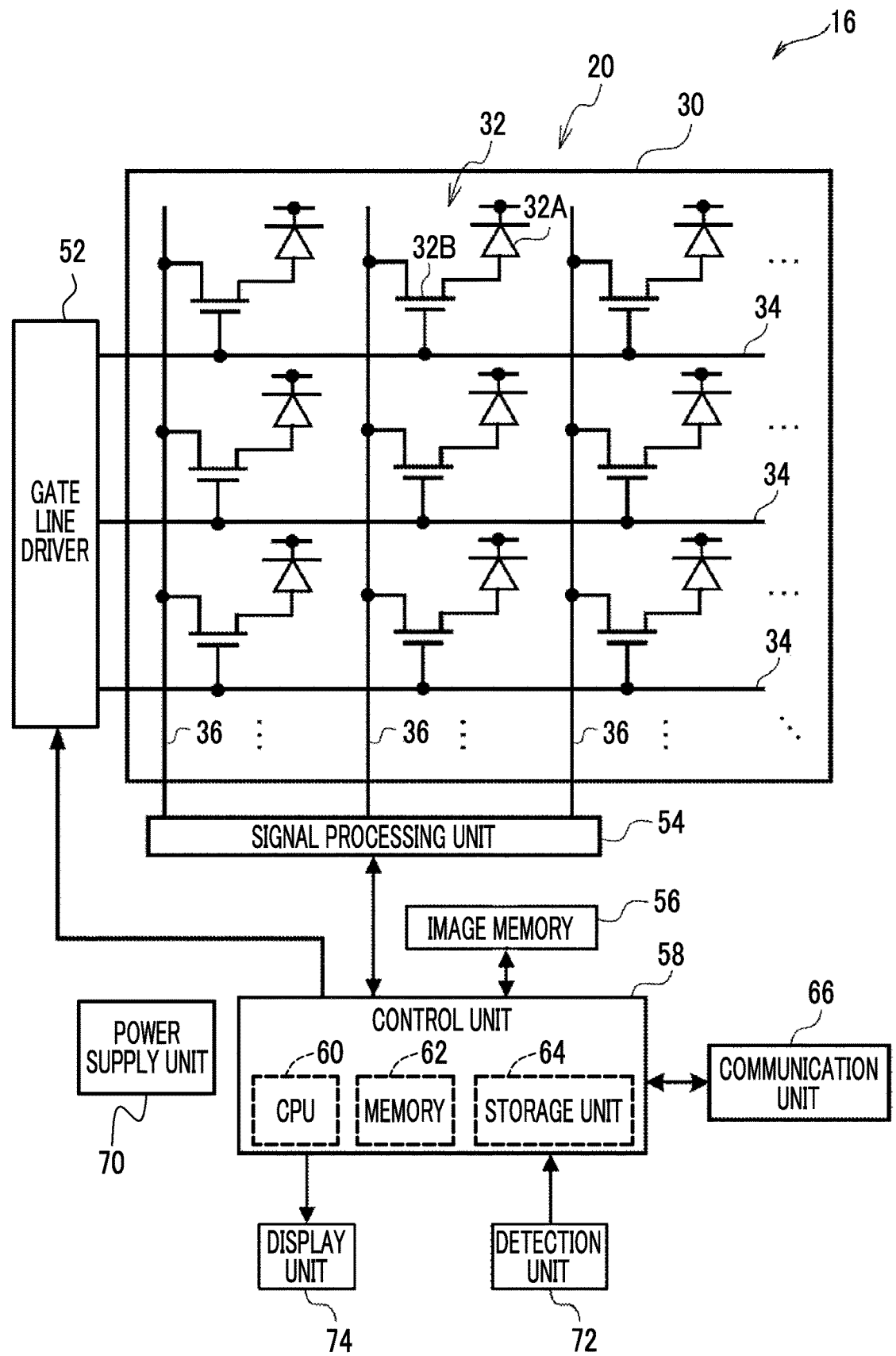
FIG. 3 is a block diagram showing an example of the configuration of a main part of an electrical system of the radiography apparatus according to the embodiment.

As shown in FIG. 3, a plurality of pixels 32 are two-dimensionally provided in one direction (a row direction in FIG. 3) and an intersection direction (a column direction in FIG. 3) that intersects the one direction in the TFT substrate 30. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs light emitted from the scintillator 22, generates charge, and accumulates the generated charge. The thin film transistor 32B converts the charge accumulated in the sensor unit 32A into an electric signal and outputs the electric signal. The sensor unit 32A is an example of a conversion element which generates a larger amount of charge as the amount of radiation becomes larger.

A plurality of gate lines 34 which extend in the one direction and are used to turn on and off each thin film transistor 32B are provided in the TFT substrate 30. In addition, a plurality of data lines 36 which extend in the intersection direction and are used to read out charge through the thin film transistors 32B in an on state are provided in the TFT substrate 30.

A gate line driver 52 is disposed on one side of two adjacent sides of the TFT substrate 30 and a signal processing unit 54 is provided on the other side. Each gate line 34 of the TFT substrate 30 is connected to the gate line driver 52, and each data line 36 of the TFT substrate 30 is connected to the signal processing unit 54.

Each row of the thin film transistors 32B of the TFT substrate 30 is sequentially turned on by an electric signal which is supplied from the gate line driver 52 through the gate lines 34. The charge read out by the thin film transistor 32B in an on state is transmitted as an electric signal through the data line 36 and is input to the signal processing unit 54. Accordingly, the charge is sequentially read out from each row of the thin film transistors and image data indicating a two-dimensional radiographic image is acquired.

The signal processing unit 54 comprises an amplifier circuit for amplifying an electric signal to be input and a sample and hold circuit (both not shown) for each data line 36, and the electric signal transmitted through each data line 36 is amplified by the amplifier circuit and then held in the sample and hold circuit. A multiplexer and an analog and digital (A/D) converter are sequentially connected to the output side of the sample and hold circuit. Then, the electric signals held in the individual sample and hold circuits are sequentially (serially) input to the multiplexer, and the electric signals sequentially selected by the multiplexer are converted into digital image data by the A/D converter.

A control unit 58 described below is connected to the signal processing unit 54, and the pieces of image data output from the A/D converter of the signal processing unit 54 are sequentially output to the control unit 58. The image memory 56 is connected to the control unit 58, and the image data sequentially output from the signal processing unit 54 is sequentially stored in the image memory 56 under the control of the control unit 58. The image memory 56 has a storage capacity capable of storing the predetermined number of pieces of image data, and image data obtained by imaging is sequentially stored in the image memory 56 every time the imaging of the radiographic image is performed.

The control unit 58 comprises a central processing unit (CPU) 60, a memory 62 including, for example, a read only memory (ROM) and a random access memory (RAM), and a non-volatile storage unit 64 such as a flash memory. The CPU 60 executes a program stored in advance in the memory 62 to perform various pieces of processing. As one example, a display processing program is stored, and the display processing program is executed to perform display processing described below. An example of the control unit 58 is a microcomputer.

A communication unit 66 is connected to the control unit 58, and transmits and receives various kinds of information to and from external apparatuses, such as the radiation emitting apparatus 12 and the console 18, using at least one of wireless communication or wired communication. The power supply unit 70 supplies power to the above-mentioned various circuits or elements (for example, the gate line driver 52, the signal processing unit 54, the image memory 56, the control unit 58, and the communication unit 66). In FIG. 3, lines for connecting the power supply unit 70 to various circuits and elements are not illustrated in order to avoid complication.

A detection unit 72 detects the up and down directions of the radiation detector 20 corresponding to the top and bottom direction of the radiographic image in a case where the radiographic image obtained by irradiating the radiation detector 20 with radiation is displayed. Specifically, the posture of the radiography apparatus 16 is detected to detect at least one direction of the upward or downward direction of the radiation detector 20. The detection unit 72 detects the posture of the radiography apparatus 16 by using an acceleration sensor such as a gyro sensor or a geomagnetic sensor. The posture of the radiography apparatus 16 includes the posture at the time of standing position imaging and the posture at the time of lying position imaging. At the time of standing position imaging, the detection unit 72 detects an orientation of the radiography apparatus 16 with respect to the direction of gravity. On the other hand, at the time of lying position imaging, the detection unit 72 detects an orientation of the radiography apparatus 16 in the horizontal direction. Since the detection unit 72 can detect the orientation in which a side serving as a predetermined reference faces at the time of lying position imaging, it is possible to determine whether the radiography apparatus 16 is disposed in the correct direction and performs the imaging by registering in advance the orientation of a patient or a bed in the control unit 58. In the disclosure, the up and down directions (upward and downward directions) in the radiography apparatus 16 and the radiation detector 20 refer to directions corresponding to the directions of the top and bottom in a case where the captured radiographic image is displayed.

Figure 4:
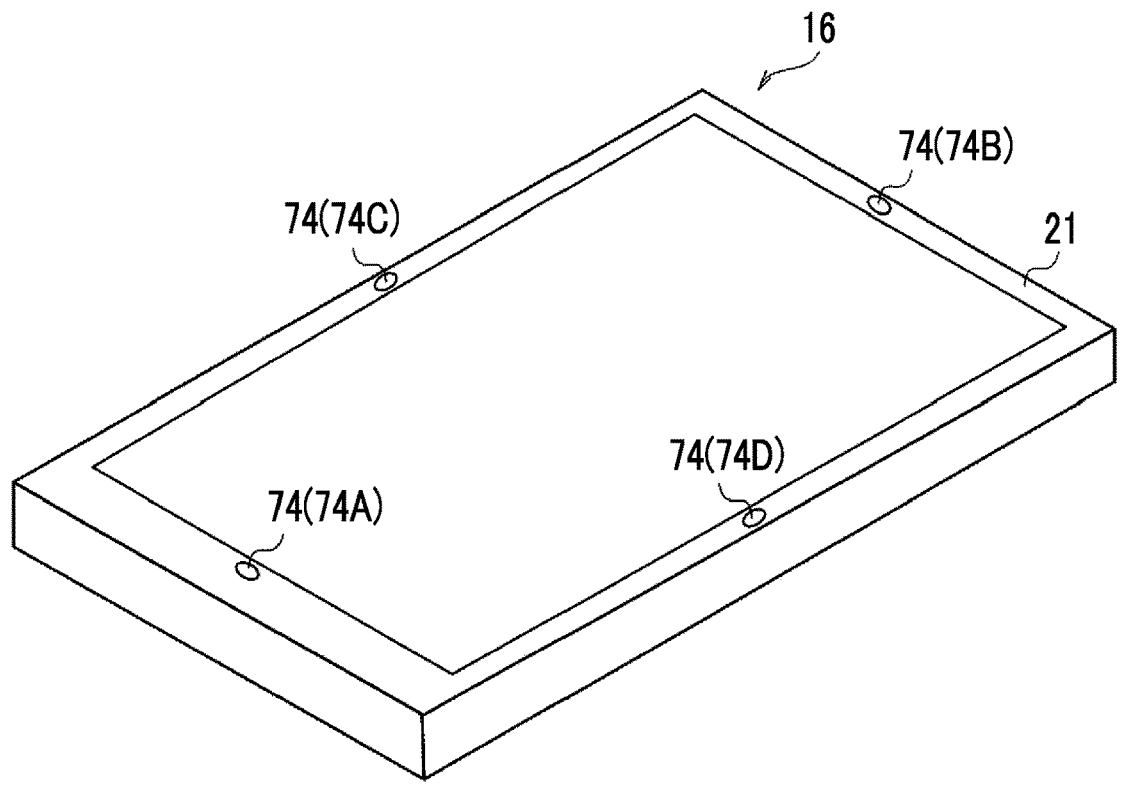
FIG. 4 is a perspective view of an appearance of the radiography apparatus according to the embodiment.

The display unit 74 displays direction information representing at least one direction of the upward or downward direction of the radiation detector 20 from the posture of the radiography apparatus 16 detected by the detection unit 72. That is, the information in the up and down directions of the radiation detector 20 corresponding to the top and bottom direction of the radiographic image obtained by irradiating the radiation detector 20 with radiation is displayed. For example, as shown in FIG. 4, light sources such as light emitting diodes (LEDs) are respectively provided, as the display units 74, corresponding to four sides of the housing 21 of the radiography apparatus 16 or two adjacent sides that may be the upward or downward direction in a case where the radiographic image is displayed to display the information in the up and down directions of the radiation detector 20. Specifically, in the case where the radiographic image is displayed, a display unit (light source) 74 in a direction which is the upward direction or a display unit (light source) 74 in a direction which is the downward direction is turned on. In this manner, the upward or downward direction of the radiography apparatus 16 with respect to the top and bottom direction of the radiographic image can be notified. FIG. 4 shows an example in which display units 74A to 74D are provided on the four sides, but the display units may be provided on only two adjacent sides. In addition, FIG. 4 shows an example in which the display units 74 are provided on a surface side to which the radiation is emitted, but the invention is not limited thereto. For example, the display units 74 may be provided on a side surface of the housing 21 of the radiography apparatus 16 which is a surface orthogonal to the surface to which the radiation is emitted. In addition, the light source is employed as the display unit 74 in this embodiment, but the display unit is not limited to the light source and a display apparatus such as a liquid crystal may be employed. In addition, FIG. 4 shows an example in which the shape of the surface to which the radiation of the radiography apparatus 16 is emitted is a rectangle, but the shape thereof is not limited to the rectangle and may be, for example, a square.

With the above configuration, the radiography apparatus 16 according to this embodiment performs the imaging of the radiographic image using a first radiation detector 20.

Figure 5:
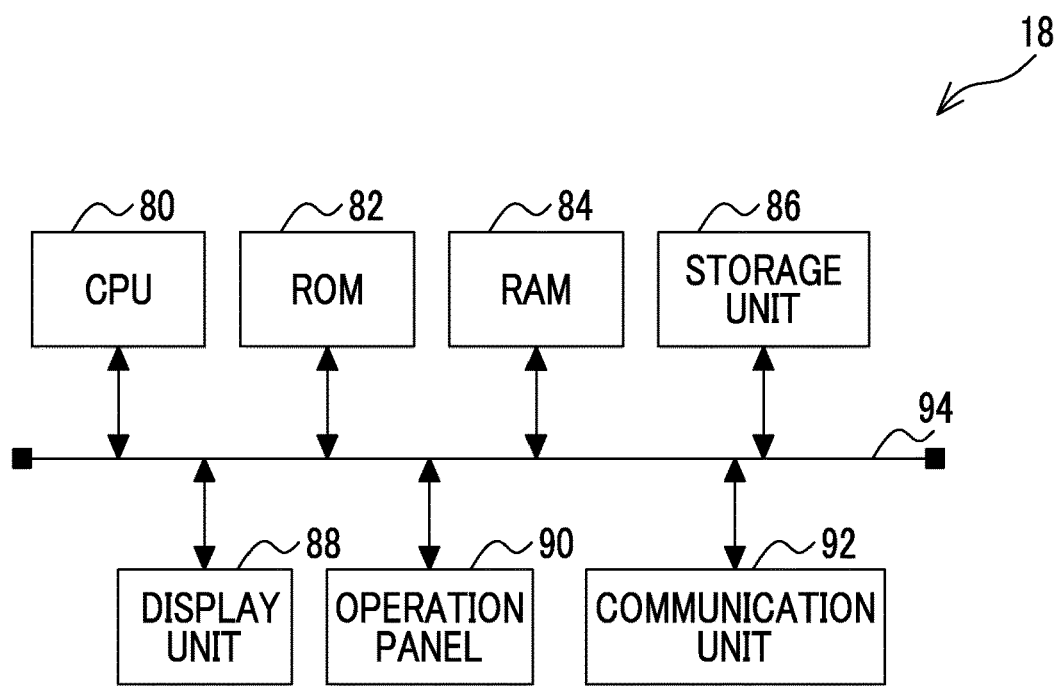
FIG. 5 is a block diagram showing an example of the configuration of a main part of an electrical system of a console according to the embodiment.

Next, the configuration of the console 18 according to this embodiment will be described with reference to FIG. 5. As shown in FIG. 5, the console 18 comprises a CPU 80 that controls the overall operation of the console 18 and a ROM 82 in which, for example, various programs and various parameters are stored in advance. In addition, the console 18 comprises a RAM 84 that is used as, for example, a work area in a case where the CPU 80 executes various programs and a non-volatile storage unit 86 such as a hard disk drive (HDD).

In addition, the console 18 comprises a display unit 88 that displays, for example, an operation menu and a radiographic image obtained by the imaging and an operation panel 90 which includes a plurality of keys and to which various kinds of information or an operation instruction such as registration of an imaging menu are input. In addition, the console 18 comprises a communication unit 92 that transmits and receives various kinds of information to and from external apparatuses, such as the radiation emitting apparatus 12 and the radiography apparatus 16, using at least one of wireless communication or wired communication. The CPU 80, the ROM 82, the RAM 84, the storage unit 86, the display unit 88, the operation panel 90, and the communication unit 92 are connected to each other through a bus 94.

However, in a case where the imaging is free imaging such as a round visit instead of the imaging on an imaging table, the direction of the radiography apparatus 16 varies depending on a state of a patient or a bed, an imaging site, or the like. There may be a case where the top and bottom of the captured radiographic image is upside down, is rotated 90 degrees, or the like, depending on the orientation of the radiography apparatus 16 at the time of imaging. Therefore, in this embodiment, the control unit 58 performs the display processing of displaying the direction of the radiography apparatus 16.

Specifically, in the display processing, the detection unit 72 detects the posture of the radiography apparatus 16 and displays direction information representing at least one direction of the upward or downward direction of the radiation detector 20 based on the detection result on the display unit 74. Accordingly, the technician can confirm the orientation of the radiography apparatus 16 by confirming the direction information displayed on the display unit 74 of the radiography apparatus 16, and thus the usability is improved.

In addition, in a case where the direction of the radiography apparatus 16 is mistakenly disposed and imaged, the control unit 58 transmits posture information representing the posture of the radiography apparatus 16 detected by the detection unit 72 to the console 18 by adding the posture information to the captured radiographic image. Alternatively, the control unit 58 transmits rotation instruction information based on the posture information to the console 18 by adding the rotation instruction information to the radiographic image. Accordingly, the console 18 can rotate the radiographic image in the correct direction using the posture information or the rotation instruction information and display the rotated radiographic image on the display unit 88.

Next, the operation of the radiography system 10 according to this embodiment will be described with reference to FIGS. 6 to 12.

First, a specific processing example of the above display processing performed by the control unit 58 of the radiography apparatus 16 according to this embodiment will be described. Hereinafter, a first example to a fifth example will be described as examples of the display processing, but the invention is not limited thereto. For example, the first example to the fifth example may be combined as appropriate.

Figure 6:
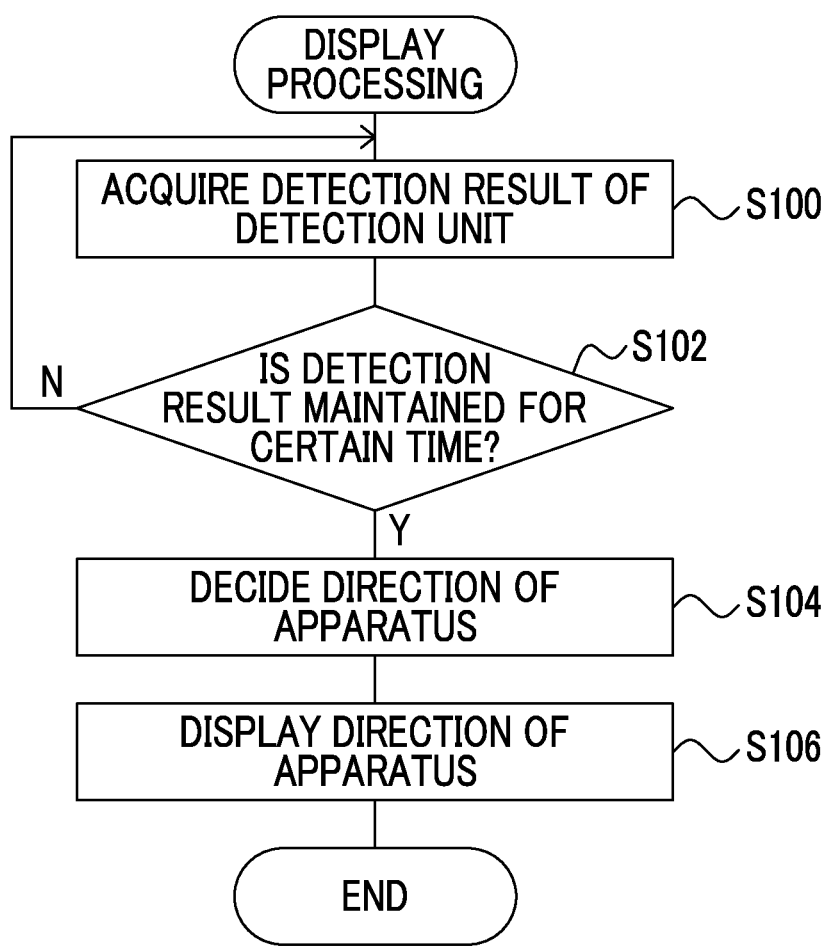
FIG. 6 is a flowchart showing a flow of a first example of display processing performed by a control unit of the radiography apparatus according to the embodiment.

FIG. 6 is a flowchart showing a flow of the first example of the display processing performed by the control unit 58 of the radiography apparatus 16 according to this embodiment. The display processing of FIG. 6 starts, for example, in a case where the power of the radiography apparatus 16 is turned on. In addition, after the power thereof is turned on and then the display processing is performed once, the processing may be started in a case where the detection result of the detection unit 72 changes after the direction of the radiography apparatus 16 is displayed on the display unit 74.

In step S100, the control unit 58 acquires the detection result of the detection unit 72 and the processing shifts to step S102.

In step S102, the control unit 58 determines whether the detection result of the detection unit 72 is maintained for a certain time. In the determination, it is determined whether the posture of the radiography apparatus 16 detected by the detection unit 72 is maintained for a predetermined time. The processing returns to step S100 to repeat the above processing in a case where the determination is negative, and the processing shifts to step S104 in a case where the determination is affirmative.

In step S104, the control unit 58 decides the direction of the radiography apparatus 16 from the detection result of the detection unit 72 and the processing shifts to step S106. That is, the orientation of the radiography apparatus 16 is determined from the posture of the radiography apparatus 16 detected by the detection unit 72, and the direction of the radiography apparatus 16 is decided.

In step S106, the control unit 58 displays the direction of the radiography apparatus 16 on the display unit 74 and the series of display processing ends. In this embodiment, the light source (the display unit 74) provided on the side, which is the upward or downward direction of the radiography apparatus 16, imaged by the radiography apparatus 16 is turned on. Accordingly, the technician can confirm the upward or downward direction of the radiographic image by confirming a position where the light source (the display unit 74) is turned on. In addition, in a case where both a vertically-long radiographic image and a horizontally-long radiographic image can be imaged with respect to a patient, light sources (the display units 74) provided on the sides which are the upward or downward direction of the radiographic images in both cases are turned on. In this manner, it is possible to confirm the upward or downward direction of the radiography apparatus 16 in both cases.

Figure 7:
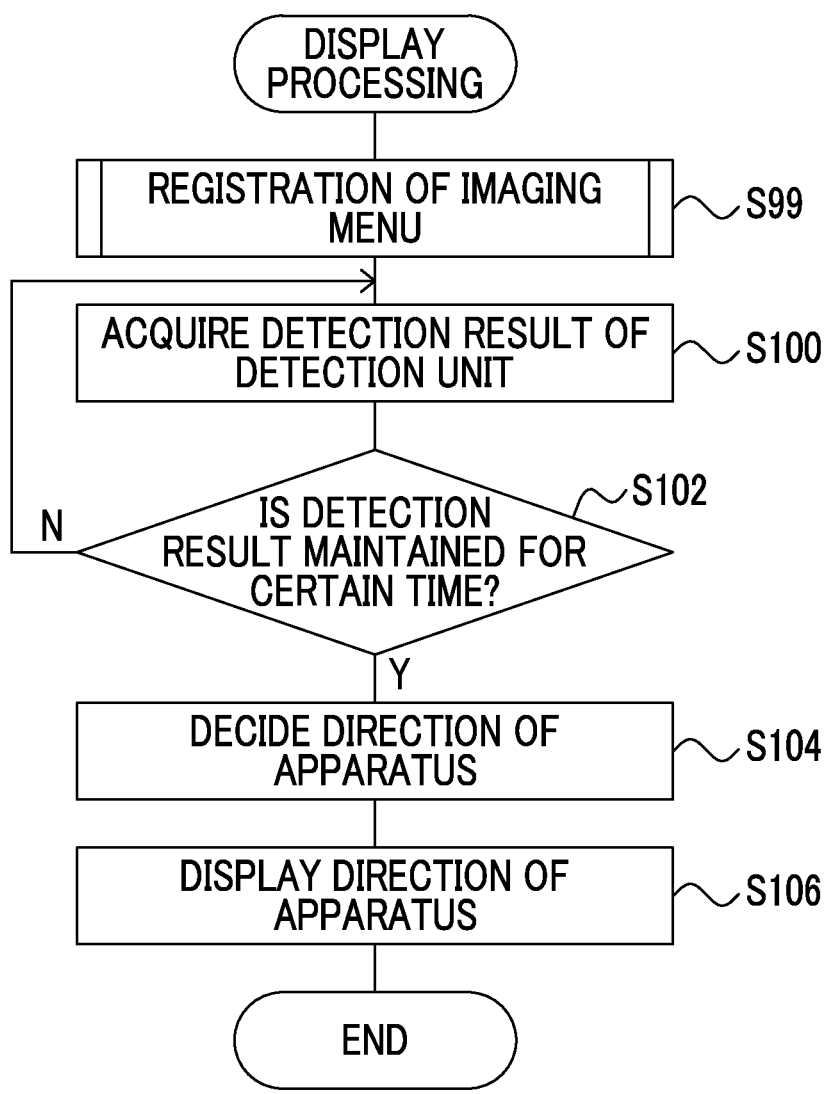
FIG. 7 is a flowchart showing a flow of a second example of the display processing performed by the control unit of the radiography apparatus according to the embodiment.

FIG. 7 is a flowchart showing a flow of the second example of the display processing performed by the control unit 58 of the radiography apparatus 16 according to this embodiment. The display processing of FIG. 7 starts, for example, in the case where the power of the radiography apparatus 16 is turned on. In addition, after the power is turned on and then the display processing is performed once, the processing may be started in a case where a change in the imaging menu is notified from the console 18. In addition, the same processing as that in FIG. 6 will be described with the same reference numeral.

In step S99, the control unit 58 performs registration processing of the imaging menu and the processing shifts to step S100. In the imaging menu registration processing, for example, the imaging menu registered from the console 18 is acquired in a case where the console 18 accepts the imaging menu. Here, as the imaging menu to be acquired, information for specifying which direction of the radiography apparatus 16 is the upward or downward direction of the radiographic image is acquired. In other words, information for specifying whether the long side of the radiography apparatus 16 is disposed along the patient for imaging or the short side of the radiography apparatus 16 is disposed along the patient for imaging is acquired.

In step S100, the control unit 58 acquires the detection result of the detection unit 72 and the processing shifts to step S102.

In step S102, the control unit 58 determines whether the detection result of the detection unit 72 is maintained for a certain time. In the determination, it is determined whether the posture of the radiography apparatus 16 detected by the detection unit 72 is maintained for a predetermined time. The processing returns to step S100 to repeat the above processing in a case where the determination is negative, and the processing shifts to step S104 in a case where the determination is affirmative.

In step S104, the control unit 58 decides the direction of the radiography apparatus 16 from the detection result of the detection unit 72 and the processing shifts to step S106. That is, the orientation of the radiography apparatus 16 is determined from the posture of the radiography apparatus 16 detected by the detection unit 72, and the direction of the radiography apparatus 16 is decided.

In step S106, the control unit 58 displays the direction of the radiography apparatus 16 on the display unit 74 and the series of display processing ends. In this embodiment, the light source (the display unit 74) which is the upward or downward direction with respect to the top and bottom direction of the radiographic image is turned on according to the registered imaging menu. For example, in the case where the long side of the radiography apparatus 16 is disposed along the patient and imaged, the short side of the radiography apparatus 16 is the upward or downward direction with respect to the radiographic image. Therefore, the light source (the display unit 74) which is provided on the short side and is in the direction which is the upward or downward direction with respect to the top and bottom direction of the radiographic image is turned on. In addition, in the case where the short side of the radiography apparatus 16 is disposed along the patient and imaged, the long side of the radiography apparatus 16 is the upward or downward direction with respect to the radiographic image. Therefore, the light source (the display unit 74) which is provided on the long side and is in the direction which is the upward or downward direction with respect to the top and bottom direction of the radiographic image is turned on. Accordingly, the technician can easily confirm the upward or downward direction of the radiographic image by confirming a position where the light source (the display unit 74) is turned on.

Figure 8:
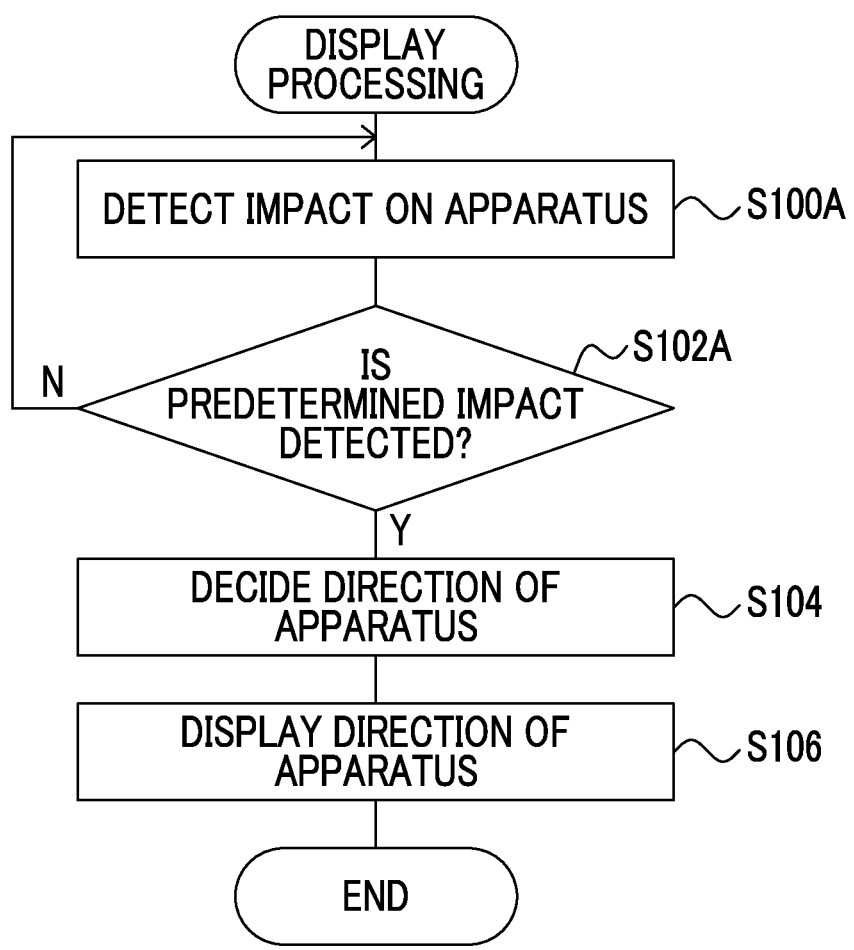
FIG. 8 is a flowchart showing a flow of a third example of the display processing performed by the control unit of the radiography apparatus according to the embodiment.

FIG. 8 is a flowchart showing a flow of a third example of the display processing performed by the control unit 58 of the radiography apparatus 16 according to this embodiment. The display processing of FIG. 8 starts, for example, in the case where the power of the radiography apparatus 16 is turned on. In addition, after the power is turned on and then the display processing is performed once, the processing may be started in a case where the detection unit 72 detects an impact. In a case where the impact is detected and the processing is started, the processing starts from step S102A described below. In addition, the same processing as that in FIG. 6 will be described with the same reference numeral.

In step S100A, the control unit 58 detects an impact on the radiography apparatus 16 and the processing shifts to step S102A. For example, the detection unit 72 detects acceleration other than the posture to detect the impact on the radiography apparatus 16. Step S100A corresponds to an impact detection unit.

In step S102A, it is determined whether the control unit 58 detects a predetermined impact. In the determination, for example, it may be determined whether an impact equal to or larger than a predetermined threshold value is detected. Alternatively, it may be determined whether an impact equal to or larger than the predetermined threshold value is detected the predetermined number of times or the predetermined number of times or more within a predetermined time. The processing returns to step S100A to repeat the above processing in a case where the determination is negative, and the processing shifts to step S104 in a case where the determination is affirmative.

In step S104, the control unit 58 decides the direction of the radiography apparatus 16 from the detection result of the detection unit 72 and the processing shifts to step S106. That is, the orientation of the radiography apparatus 16 is determined from the posture of the radiography apparatus 16 detected by the detection unit 72, and the direction of the radiography apparatus 16 is decided.

In step S106, the control unit 58 displays the direction of the radiography apparatus 16 on the display unit 74 and the series of display processing ends. In this embodiment, the light source (the display unit 74) provided on the side, which is the upward or downward direction of the radiography apparatus 16, imaged by the radiography apparatus 16 is turned on. Accordingly, the technician can confirm the upward or downward direction of the radiographic image by confirming a position where the light source (the display unit 74) is turned on. In addition, in a case where both a vertically-long radiographic image and a horizontally-long radiographic image can be imaged with respect to a patient, light sources (the display units 74) provided on the sides which are the upward or downward direction of the radiographic images in both cases are turned on. In this manner, it is possible to confirm the upward or downward direction of the radiography apparatus 16 in both cases.

Figure 9:
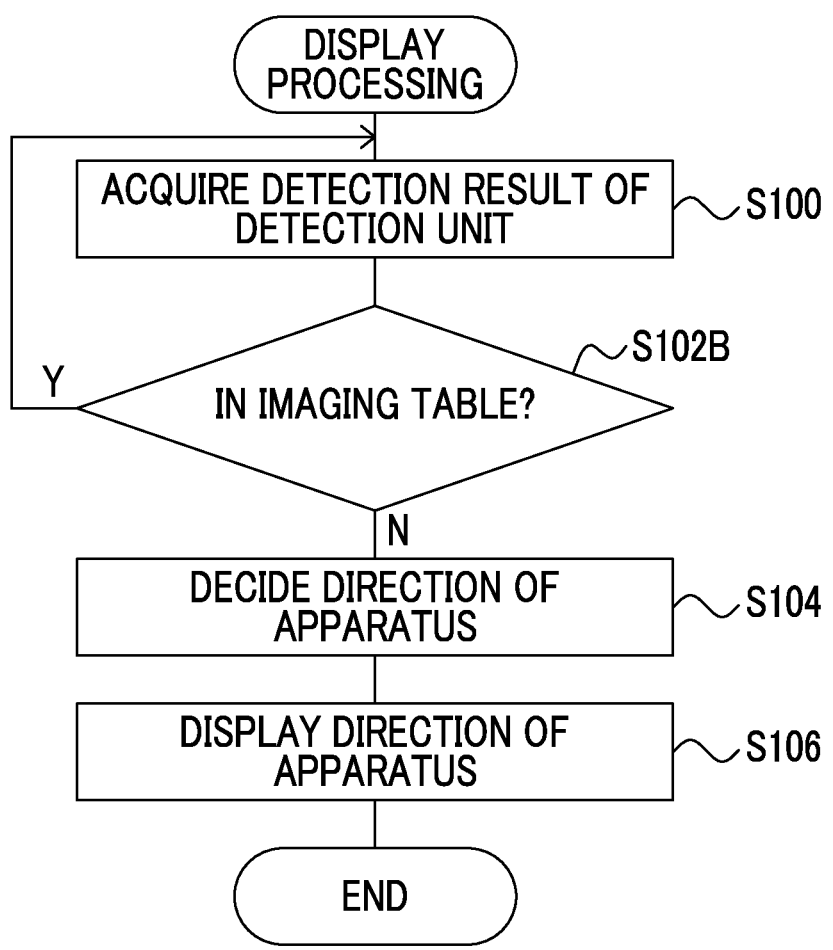
FIG. 9 is a flowchart showing a flow of a fourth example of the display processing performed by the control unit of the radiography apparatus according to the embodiment.

FIG. 9 is a flowchart showing a flow of a fourth example of the display processing performed by the control unit 58 of the radiography apparatus 16 according to this embodiment. The display processing of FIG. 9 starts, for example, in the case where the power of the radiography apparatus 16 is turned on. In addition, the same processing as that in FIG. 6 will be described with the same reference numeral.

In step S100, the control unit 58 acquires the detection result of the detection unit 72 and the processing shifts to step S102B.

In step S102B, the control unit 58 determines whether the radiography apparatus 16 is in the imaging table. In the determination, for example, information on technique selection (for example, selection of whether the imaging is the free imaging or the imaging on the imaging table at imaging menu registration) from the console 18 is acquired, and it is determined whether the radiography apparatus 16 is in the imaging table based on the acquired information. Alternatively, a sensor, a switch or the like that detects that the radiography apparatus 16 is disposed in the imaging table is provided, and the determination is made based on a detection result of the sensor or a state of the switch. The processing returns to step S100 to repeat the above processing in a case where the determination is affirmative, and the processing shifts to step S104 in a case where the determination is negative. That is, in a case where the radiography apparatus 16 is installed on the imaging table, the following processing is not performed and the display of the display unit is prohibited.

In step S104, the control unit 58 decides the direction of the radiography apparatus 16 from the detection result of the detection unit 72 and the processing shifts to step S106. That is, the orientation of the radiography apparatus 16 is determined from the posture of the radiography apparatus 16 detected by the detection unit 72, and the direction of the radiography apparatus 16 is decided.

In step S106, the control unit 58 displays the direction of the radiography apparatus 16 on the display unit 74 and the series of display processing ends. In this embodiment, the light source (the display unit 74) provided on the side, which is the upward or downward direction of the radiography apparatus 16, imaged by the radiography apparatus 16 is turned on. Accordingly, the technician can confirm the upward or downward direction of the radiographic image by confirming a position where the light source (the display unit 74) is turned on. In addition, in a case where both a vertically-long radiographic image and a horizontally-long radiographic image can be imaged with respect to a patient, light sources (the display units 74) provided on the sides which are the upward or downward direction of the radiographic images in both cases are turned on. In this manner, it is possible to confirm the upward or downward direction of the radiography apparatus 16 in both cases.

Figure 10:
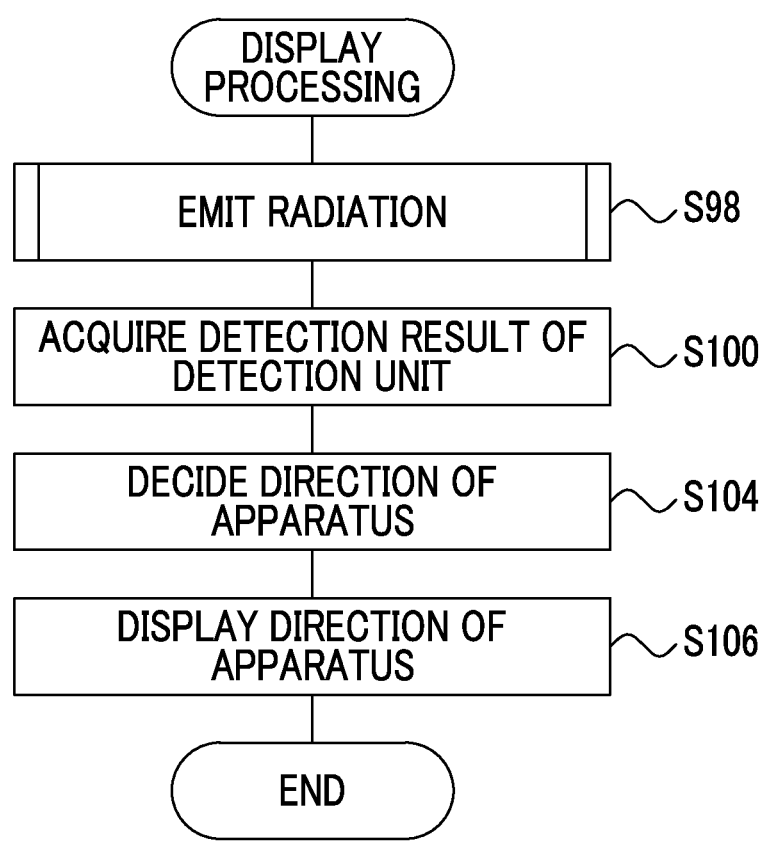
FIG. 10 is a flowchart showing a flow of a fifth example of the display processing performed by the control unit of the radiography apparatus according to the embodiment.

FIG. 10 is a flowchart showing a flow of a fifth example of the display processing performed by the control unit 58 of the radiography apparatus 16 according to this embodiment. The display processing of FIG. 10 starts, for example, in the case where the power of the radiography apparatus 16 is turned on. In addition, the same processing as that in FIG. 6 will be described with the same reference numeral.

In step S98, the control unit 58 performs emission processing of the radiation and the processing shifts to step S100. In the emission processing of the radiation, for example, in a case where the radiation emitting apparatus 12 comprises the irradiation button or the like, an instruction to emit the radiation R is received by the irradiation button. In addition, for example, in a case where the console 18 is operated to perform the instruction to emit the radiation R, the instruction to emit the radiation R is received from the console 18. Alternatively, in a case where the radiation detector 20 has a function of detecting the radiation R, the radiation detector 20 may perform processing of detecting the emission of the radiation.

In step S100, the control unit 58 acquires the detection result of the detection unit 72 and the processing shifts to step S104.

In step S104, the control unit 58 decides the direction of the radiography apparatus 16 from the detection result of the detection unit 72 and the processing shifts to step S106. That is, the orientation of the radiography apparatus 16 is determined from the posture of the radiography apparatus 16 detected by the detection unit 72, and the direction of the radiography apparatus 16 is decided.

In step S106, the control unit 58 displays the direction of the radiography apparatus 16 on the display unit 74 and the series of display processing ends. In this embodiment, the light source (the display unit 74) provided on the side, which is the upward or downward direction of the radiography apparatus 16, imaged by the radiography apparatus 16 is turned on. Accordingly, the technician can confirm the upward or downward direction of the radiographic image by confirming a position where the light source (the display unit 74) is turned on. In addition, in a case where both a vertically-long radiographic image and a horizontally-long radiographic image can be imaged with respect to a patient, light sources (the display units 74) provided on the sides which are the upward or downward direction of the radiographic images in both cases are turned on. In this manner, it is possible to confirm the upward or downward direction of the radiography apparatus 16 in both cases.

Figure 11:
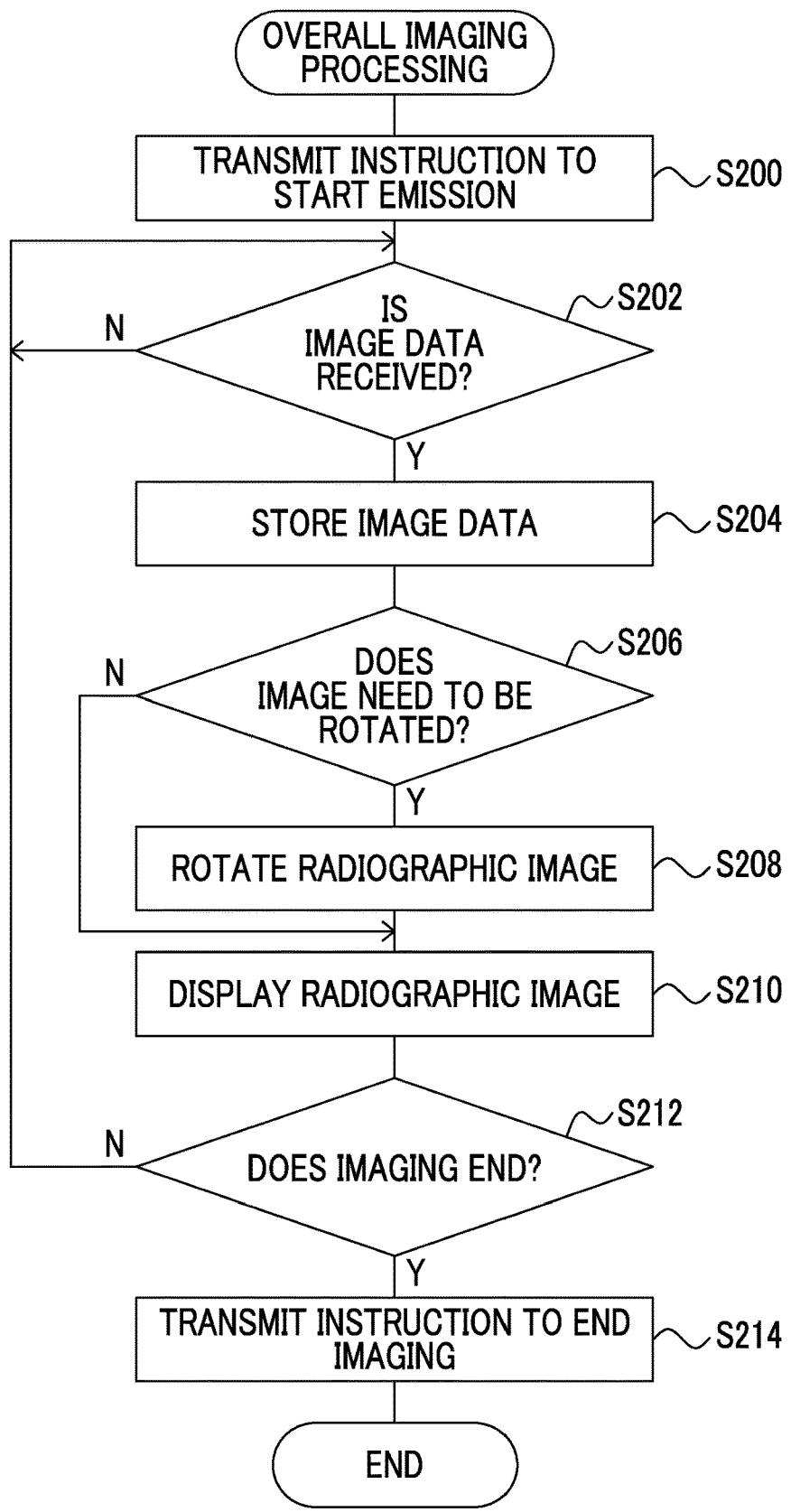
FIG. 11 is a flowchart showing a flow of processing of the overall imaging processing program executed by a CPU of the console.

FIG. 11 is a flowchart showing a flow of processing of an overall imaging processing program executed by the CPU 80 of the console 18 in a case where the user inputs an imaging menu including, for example, a name of the subject W, an imaging site, and an imaging condition through the operation panel 90. The overall imaging processing program is installed in the ROM 82 of the console 18 in advance. The imaging condition includes, for example, emission conditions, such as a tube voltage, a tube current, and one pulse emission period which are set to the radiation emitting apparatus 12, information indicating an imaging mode, and a frame rate.

Figure 12:
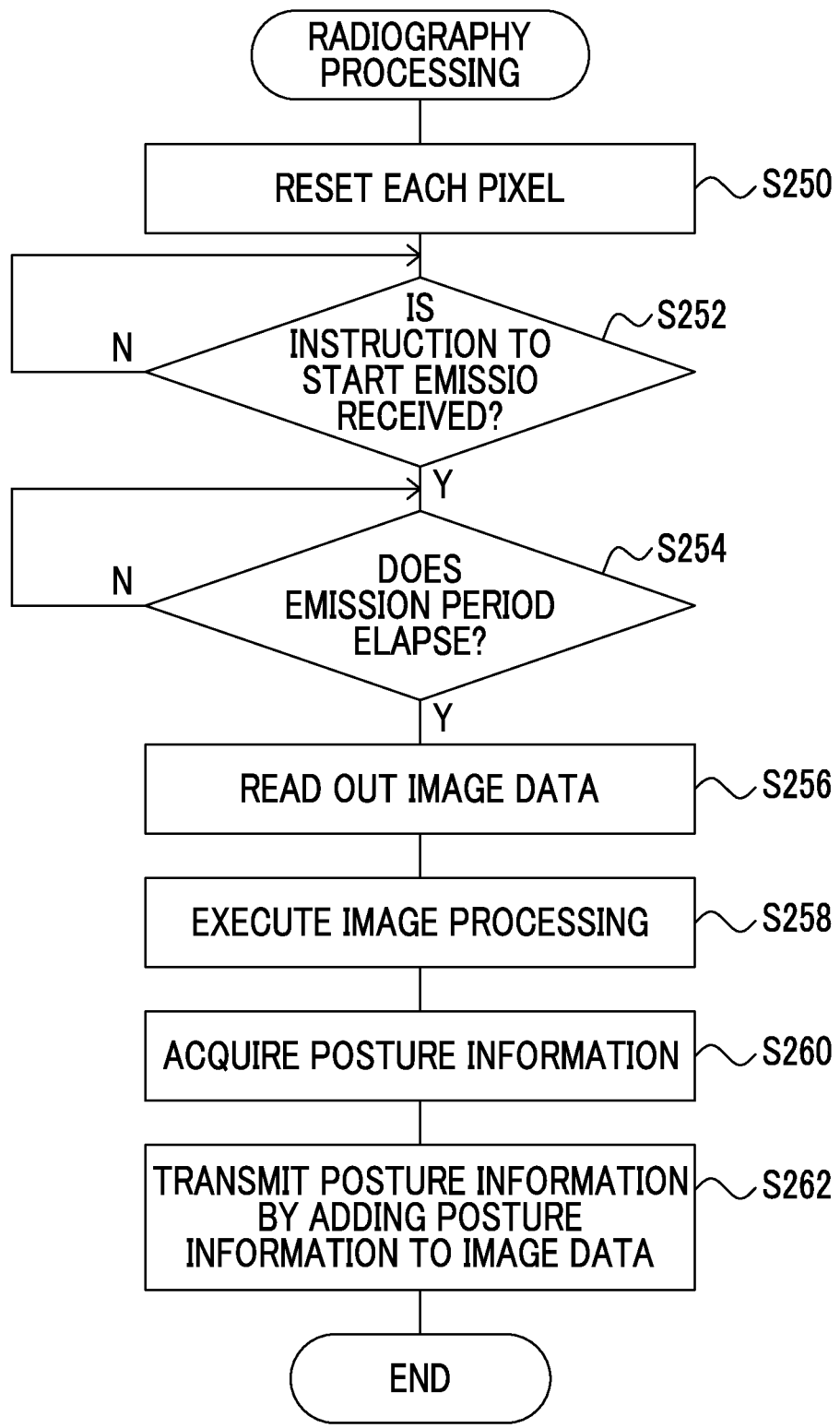
FIG. 12 is a flowchart showing a flow of processing of a radiography processing program executed by the control unit of the radiography apparatus according to the embodiment.

FIG. 12 is a flowchart showing a flow of processing of a radiography processing program executed by the control unit 58 of the radiography apparatus 16 after the power switch of the radiography apparatus 16 is in an on state and then the above display processing is performed. In addition, the radiography processing program is installed in a ROM of the memory 62 of the control unit 58 in advance.

In step S200 of FIG. 11, the CPU 80 of the console 18 transmits information included in the input imaging menu to the radiography apparatus 16 through the communication unit 92 and transmits the emission conditions of the radiation R to the radiation emitting apparatus 12 through the communication unit 92. Then, the CPU 80 transmits an instruction to start the emission of the radiation R to the radiography apparatus 16 and the radiation emitting apparatus 12 through the communication unit 92. In a case of receiving the emission conditions and the emission start instruction transmitted from the console 18, the radiation emitting apparatus 12 emits the radiation R in a pulse shape according to the received emission conditions. In the case where the radiation emitting apparatus 12 comprises the irradiation button, the radiation emitting apparatus 12 receives the emission conditions and the emission start instruction transmitted from the console 18 and emits the radiation R in a pulse shape according to the received emission conditions in a case where the irradiation button is pressed.

Next, in step S202, it is determined whether the CPU 80 receives the image data transmitted by the radiography apparatus 16 as described below. It waits until the determination is affirmative, and the processing shifts to step S204. In a case where the CPU 80 receives the image data transmitted by the radiography apparatus 16, the determination result in step S202 becomes affirmative and the processing shifts to step S204.

In step S204, the CPU 80 stores the image data received in step S202 in the storage unit 86 and the processing shifts to step S206.

In step S206, the CPU 80 determines whether the image needs to be rotated. In this determination, it is determined whether the above posture information or rotation instruction information is added to the image data received from the radiography apparatus 16. The processing shifts to step S208 in a case where the determination is affirmative, and the processing shifts to step S210 in a case where the determination is negative.

In step S208, the CPU 80 rotates the radiographic image represented by the image data using the posture information or the rotation instruction information and the processing shifts to step S210.

In step S210, the CPU 80 displays the radiographic image indicated by the image data on the display unit 88 and the processing shifts to step S212. Here, since the radiographic image displayed on the display unit 88 is rotated using the posture information or the rotation instruction in a case where the radiographic image needs to be rotated, it is possible to display the top and bottom of the radiographic image as the normal position without displaying the top and bottom of the radiographic image upside down or in a rotated manner.

In step S212, the CPU 80 determines whether it is time to end the imaging. Examples of the time of ending the imaging include a time at which an instruction to end the imaging is input by the user through the operation panel 90 and a time at which the irradiation button is pressed again. The processing returns to step S202 described above in a case where the determination in step S212 is negative, and the processing shifts to step S214 in a case where the determination is affirmative.

In step S214, the CPU 80 transmits the instruction to end the imaging to the radiography apparatus 16 and the radiation emitting apparatus 12 through the communication unit 92 and then ends the overall imaging processing. In a case of receiving the instruction to end the imaging transmitted from the console 18, the radiation emitting apparatus 12 ends the emission of the radiation R.

On the other hand, in step S250 of FIG. 12, the control unit 58 performs a reset operation which extracts the charge accumulated in the sensor unit 32A of each pixel 32 in the radiation detector 20 and removes the charge, and the processing shifts to step S252. The control unit 58 may perform the reset operation in step S250 only once, may repeat the reset operation the predetermined number of times, or may repeat the reset operation until the determination in step S252, as described below, becomes affirmative.

In step S252, it is determined whether the control unit 58 receives the instruction to start the emission of radiation R. It waits until the determination is affirmative, and the processing shifts to step S254. That is, in a case where the control unit 58 receives the emission start instruction transmitted from the console 18 by the processing in step S200 of the overall imaging processing through the communication unit 66, the determination in step S252 is affirmative. In the case where the radiation emitting apparatus 12 comprises the irradiation button, the determination in step S252 is affirmative in a case where the control unit 58 receives the emission start instruction transmitted from the console 18 and the information indicating that the irradiation button is pressed through the communication unit 66. In this case, for example, in the case where the irradiation button is pressed, the radiation emitting apparatus 12 may directly transmit the information indicating that the irradiation button is pressed to the radiography apparatus 16 or may transmit the information to the radiography apparatus 16 through the console 18.

In step S254, the control unit 58 determines whether the emission period included in the information transmitted from the console 18 by the processing in step S100 of the overall imaging processing elapses. It waits until the determination is affirmative, and the processing shifts to step S256.

In step S256, the control unit 58 reads out the image data and the processing shifts to step S258. That is, the control unit 58 controls the gate line driver 52 to sequentially output on signals line by line for a predetermined period from the gate line driver 52 to each gate wiring 34 of the radiation detector 20. Accordingly, the thin film transistors 32B connected to the gate lines 34 are sequentially turned on line by line, and the charges accumulated in the sensor units 32A flow out to the data lines 36 as electric signals line by line. The electric signal flowing out to each data line 36 is converted into digital image data by the signal processing unit 54 and stored in the image memory 56.

In step S258, the control unit 58 executes image processing for performing various corrections such as offset correction and gain correction on the image data stored in the image memory 56 in step S256, and the processing shifts to step S260.

In step S260, the control unit 58 acquires the posture information detected by the detection unit 72, and the processing shifts to step S262.

In step S262, the control unit 58 transmits the posture information to the console 18 through the communication unit 66 by adding the posture information to the image data subjected to the image processing in step S258, and then ends the individual imaging process. In step S262, in a case where the image data needs to be rotated from the detection result of the detection unit 72, a rotation instruction including a rotation direction and a rotation amount may be transmitted to the console 18 through the communication unit 66 by being added to the image data instead of the posture information. Step S262 corresponds to the transmission unit 17 (shown, for example, in FIG. 1), and the console 18 corresponds to the external apparatus. In addition, the posture information or the rotation instruction may be separately transmitted to the console 18 without being added to the image data.

In the first to fifth examples of the display processing in the above embodiment, the end (the turning off of the light source) of the display by the display unit 74 is not mentioned, but the display by the display unit 74 may be ended in a case where the power of the radiography apparatus 16 is turned off as the end time of the display by the display unit 74. Alternatively, the display by the display unit 74 may be ended at the time of ending the imaging (for example, in a case where the next menu is not registered). In a case where the next menu is registered at the time of ending the imaging, the displayable state may be maintained. Every time the detection unit 72 detects that the direction of the radiography apparatus 16 is changed, the display may be changed to continue the display.

The case where an indirect-conversion-type radiation detector that once converts the radiation R into light and converts the converted light into charge is employed as the radiation detector 20 is described in the above embodiment, but the invention is not limited thereto. For example, a direct-conversion-type radiation detector that directly converts the radiation R into charge may be employed as the radiation detector 20. Examples of the conversion layer that absorbs the radiation and converts the radiation into the charge in the direct-conversion-type radiation detector include amorphous selenium (a-Se) and crystalline cadmium telluride (CdTe).

The case where the penetration side sampling radiation detector in which the radiation R is incident from the scintillator 22 side is employed as the radiation detector 20 is described in the above embodiment, but the invention is not limited thereto. For example, a so-called irradiation side sampling (ISS) radiation detector in which the radiation R is emitted from the TFT substrate 30 side may be employed as the radiation detector 20.

In addition, various types of processing executed by the CPU executing software (program) in the above embodiment may be executed by various processors other than the CPU. Examples of the processor in this case include a programmable logic device (PLD) whose circuit configuration can be changed after the manufacturing such as a field-programmable gate array (FPGA) and a dedicated electric circuit which is a processor having a circuit configuration specially designed in order to execute specific processing such as an application specific integrated circuit (ASIC). In addition, the various pieces of processing described above may be executed by one of these various processors, or a combination of two or more processors of the same or different types (for example, a plurality of FPGAs or a combination of a CPU and an FPGA). In addition, a hardware structure of these various processors is, more specifically, an electric circuit combining circuit elements such as a semiconductor element.

The overall imaging processing program is stored (installed) in the storage unit 86 in advance in the above embodiment, but the invention is not limited thereto. The overall imaging processing program may be provided in a form of being recorded on a recording medium such as a compact disk read only memory (CD-ROM), a digital versatile disk read only memory (DVD-ROM), or a universal serial bus (USB) memory. In addition, the overall imaging processing program may be downloaded from an external information processing apparatus or the like through a network.

The individual imaging processing program and the display processing program are stored in the ROM of the memory 62 of the control unit 58 in advance in the above embodiment, but the invention is not limited thereto. The individual imaging processing program may be provided in a form of being recorded on the recording medium. In addition, the individual imaging processing program and the display processing program may be downloaded from an external information processing apparatus or the like through a network.

The configuration, the operation, and the like of the radiography system 10 described in the above embodiment are merely examples, and it goes without saying that the changes can be made depending on the situation within the scope not departing from the spirit of the disclosure.

What is claimed is:

1. A radiography apparatus comprising:
a radiation detector that generates and outputs image data representing a radiographic image corresponding to emitted radiation, and up and down directions of the radiation detector are set in an advance with respect to top and bottom directions of the radiographic image;
a housing that accommodates the radiation detector;
a direction detector that detects at least one direction of the up or down directions of the radiation detector; and
a light source that is provided in the housing and displays direction information representing the at least one direction of the up and down directions of the radiation detector detected by the direction detector.

2. The radiography apparatus according to claim 1, further comprising:
a controller that performs a control to display the direction information on the light source in a case where a direction of the housing does not change at least for a predetermined time.

3. The radiography apparatus according to claim 1, further comprising:
a controller that performs a control to display the direction information on the light source in a case where a registration of an imaging menu is accepted.

4. The radiography apparatus according to claim 1, further comprising:
an impact detector that detects an impact; and
a controller that performs a control to display the direction information on the light source in a case where a predetermined impact is detected by the impact detector.

5. The radiography apparatus according to claim 4,
wherein the predetermined impact is at least one of an impact equal to or larger than a predetermined threshold value or an impact equal to or larger than a predetermined number of times.

6. The radiography apparatus according to claim 1, further comprising:
a controller that performs a control to display the direction information on the light source in a case where an emission of radiation is started.

7. The radiography apparatus according to claim 1, further comprising:
a transmitter that transmits a detection result of the direction detector to an external apparatus.

8. The radiography apparatus according to claim 7,
wherein the transmitter transmits the detection result of the direction detector to the external apparatus by adding the detection result to the image data.

9. The radiography apparatus according to claim 1, further comprising:
a transmitter that transmits a rotation instruction including a rotation direction and a rotation amount to an external apparatus in a case where the image data needs to be rotated from a detection result of the direction detector.

10. The radiography apparatus according to claim 9,
wherein the transmitter transmits the rotation instruction to the external apparatus by adding the rotation instruction to the image data.

11. The radiography apparatus according to claim 1, further comprising:
a controller that performs a control to prohibit a display of the direction information on the light source in a case where the radiography apparatus is in an imaging table.

12. A radiography method in which a computer executes processing, the radiography method comprising:

detecting by a detection unit at least one direction of up and down directions of a radiation detector that generates and outputs image data representing a radiographic image corresponding to emitted radiation, and up and down directions of the radiation detector are set in an advance with respect to top and bottom directions of the radiographic image; and displaying the at least one direction of the up and down directions of the radiation detector detected by the detection unit on a display unit provided in a housing for accommodating the radiation detector.

13. A non-transitory computer-readable storage-medium storing therein a radiography program that causes a computer to execute:

detecting by a detection unit at least one direction of up and down directions of a radiation detector that generates and outputs image data representing a radiographic image corresponding to emitted radiation, and up and down directions of the radiation detector are set in an advance with respect to the top and bottom directions of the radiographic image; and displaying the at least one direction of the up and down directions of the radiation detector detected by the detection unit on a display unit provided in a housing for accommodating the radiation detector.

* * * * *